US006959588B2

(12) United States Patent
Zougari et al.

(10) Patent No.: US 6,959,588 B2
(45) Date of Patent: Nov. 1, 2005

(54) COUETTE DEVICE AND METHOD TO STUDY SOLIDS DEPOSITION FROM FLOWING FLUIDS

(75) Inventors: Mohammed I. Zougari, Edmonton (CA); Ahmed Hammami, Edmonton (CA); Kunal Karan, Kingston (CA); Scott Jacobs, Edmonton (CA); John Ratulowski, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/465,493

(22) Filed: Jun. 19, 2003

(65) Prior Publication Data

US 2004/0255649 A1 Dec. 23, 2004

(51) Int. Cl.$^7$ .......................... G01N 33/00; G01N 25/00
(52) U.S. Cl. ........................................... 73/61.62; 374/7
(58) Field of Search ............................ 73/61.62; 374/7

(56) References Cited

U.S. PATENT DOCUMENTS

| | | | | |
|---|---|---|---|---|
| 2,644,330 A | * | 7/1953 | Jonach et al. ............... 73/61.62 |
| 3,080,747 A | * | 3/1963 | Kerst ........................ 73/61.62 |
| 4,339,945 A | * | 7/1982 | Knudsen et al. ........... 73/61.62 |
| 4,383,438 A | * | 5/1983 | Eaton ........................ 73/61.62 |
| 5,194,145 A | * | 3/1993 | Schoendorfer ............. 210/90 |
| 5,257,528 A | * | 11/1993 | Degouy et al. ............ 73/53.01 |
| 5,361,631 A | * | 11/1994 | Covington et al. ....... 73/152.24 |
| 5,470,498 A | * | 11/1995 | Pialet et al. ............... 252/76 |
| 5,531,103 A | * | 7/1996 | Eaton ........................ 73/61.62 |
| 5,780,055 A | * | 7/1998 | Habib et al. ............... 424/464 |
| 5,959,194 A |   | 9/1999 | Nenniger |
| 6,023,070 A | * | 2/2000 | Wetegrove et al. ........ 250/573 |
| 6,062,069 A | * | 5/2000 | Panchal et al. ............ 73/53.01 |
| 6,807,849 B1 | * | 10/2004 | Reed et al. ................ 73/60.11 |
| 2004/0102330 A1 | * | 5/2004 | Zhou et al. ................ 507/100 |

FOREIGN PATENT DOCUMENTS

CA 2197535 8/1998

OTHER PUBLICATIONS

Newberry, *Journal of Petroleum Technology*, pp. 779–786 (May 1984).
Lathrop et al., *The American Physical Society* 46(10):6390–6405 (Nov. 15, 1992).

* cited by examiner

Primary Examiner—Michael Cygan
(74) Attorney, Agent, or Firm—Williams, Morgan & Amerson, P.C.; Bryan P. Galloway; Jaime A. Castano (57) ABSTRACT

We disclose a method of measuring an emulsion or solids deposition in a fluid sample, comprising charging the sample to a Couette device; subjecting the sample in the Couette device to a pressure, a temperature, and a shear comparable to field conditions; changing at least one of the pressure, temperature, composition, or shear of the sample; and quantifying the type and amount of solids deposited on the interior walls of the Couette device. We also disclose Couette devices which can be used in the method.

16 Claims, 3 Drawing Sheets

COUETTE DEVICE AND METHOD TO STUDY SOLIDS DEPOSITION FROM FLOWING FLUIDS

BACKGROUND OF THE INVENTION

1. Field of the Invention

The present invention relates generally to the fields of Couette devices and methods involving their use. More particularly, it concerns Couette devices capable of imparting fully turbulent flow to samples, such as crude oil samples, for use in measuring deposition of solids from the samples.

2. Description of Related Art

In fluids which it is desirable to transport by flowing through pipes or tubing, the deposition of solids from the fluid onto the interior walls of the pipes or tubing can impair fluid flow. An example of such a fluid is crude oil. Crude oil from many formations commonly contains solids, often as one or more of waxes, asphaltenes, sulfur, scale, and hydrates.

Paraffin waxes are essentially mixtures of long-chain n-paraffins with carbon chain lengths ranging from $C_{15}$ to $C_{75+}$.

Asphaltenes and residual oil components often co-precipitate with the paraffin waxes and result in varying appearance (color) and texture to the precipitated solids. Asphaltenes are generally compounds comprising more than about 70 carbon atoms, mostly in aromatic polycyclic clusters variably substituted with alkyl groups; asphaltenes can also contain heteroatoms (such as N, S, or O), metals (such as Ni, V, or Fe), or both.

Hydrates generally comprise water molecules in an ice-like structure encaging one or more organic compounds. The organic compounds encaged by the ice-like structure are commonly methane, ethane, propane, or other alkanes with less than about 10 carbon atoms.

Under many conditions, the solids present in a fluid will remain dissolved in the fluid. However, when a fluid, such as crude oil, is transported via pipe, such as from a geologic formation to a wellhead via production tubing or from a wellhead or a storage vessel to a refinery via a pipeline, changes in the pressure, temperature, composition, or other parameters of the flowing fluid can lead to precipitation and deposition of solids. Deposition in a pipe is generally undesirable, because deposited solids can at least partially block the pipe and lead to reductions in the flow rate of the fluid in the pipe and require expensive and time-consuming cleaning of the pipe to restore the maximum flow rate of the fluid.

Similar observations exist for other fluids which can contain solids. Such fluids, either liquids or gases, include fluids used in the industrial production of paint, food products, pharmaceuticals, plastics, and paper and paper products, among other industries.

The study of deposition is difficult for, among other reasons, the difference between fully turbulent flow (that is, flow that is both non-laminar and without the presence of vortices) of a sample fluid in a pipe and the sample fluid in a laboratory scale apparatus. Common laboratory scale apparatus are generally unable to provide conditions for fully turbulent flow as a result of limitations in apparatus geometry and design. Further, common laboratory scale apparatus generally cannot provide sufficient levels of pressure and shear to readily study the deposition of solids.

Therefore, it would be desirable to have apparatus and methods for analyzing deposition of solids that can simulate the turbulent flow found in production tubing or pipeline under field conditions.

SUMMARY OF THE INVENTION

In one embodiment, the present invention relates to a method of measuring solids deposition from a fluid sample, comprising charging the sample of initial composition to a Couette device having interior walls; subjecting the sample in the Couette device to an initial pressure, an initial temperature, and an initial shear; changing at least one of the pressure, temperature, composition, or shear of the sample, or the surface type or surface roughness of the device; and quantifying deposits on the interior walls of the Couette device.

In another embodiment, the present invention relates to a device to measure deposition, comprising an outer housing; an inner housing rotatably connected to and enclosed by the outer housing, the outer housing and the inner housing defining a space therebetween; and a rotatable connector connecting the outer housing to the inner housing.

In one embodiment, the present invention relates to a method of measuring solids deposition in a sample of a fluid, comprising: charging the sample to a Couette device; subjecting the sample in the Couette device to a pressure, a temperature, and a shear comparable to field conditions; changing at least one of the pressure, temperature, composition, or shear of the sample, or the surface type or surface roughness of the device; and quantifying the type and amount of solids deposited on the interior walls of the Couette device.

In another embodiment, the present invention relates to a Couette device, comprising: an outer cylinder characterized by having a radius $r_o$; an inner cylinder, rotatably connected to and coaxial with the outer cylinder, and characterized by having a radius $r_i$, wherein $r_i<r_o$ and the outer cylinder and the inner cylinder define an annulus; and a rotatable connector connecting the outer cylinder to the inner cylinder.

In a further embodiment, the present invention relates to a method of studying an emulsion in a sample of a fluid, comprising charging the sample to a Couette device; subjecting the sample to a pressure, a temperature, and a shear comparable to field conditions; changing at least one of the pressure, temperature, composition, or shear of the sample, or the surface type or surface roughness of the device; and quantifying the type and amount of the emulsion in the sample.

In an additional embodiment, the present invention relates to an apparatus for measuring solids deposition in a sample of a fluid, comprising: means for subjecting a sample of a fluid comprising solids to turbulent flow, wherein the sample has a pressure, a temperature, a composition, and is subject to a shear; means for changing at least one of the pressure, the temperature, or the composition of the sample or the shear to which the sample is subjected; and means for measuring the deposition of the solids resulting from the change in the pressure, the temperature, the composition, or the shear.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows a side cross-sectional view of a cylindrical Couette device of the present invention.

DESCRIPTION OF ILLUSTRATIVE EMBODIMENTS

In one embodiment, the present invention relates to a Couette device, comprising:

an outer cylinder characterized by having a radius $r_o$;

an inner cylinder, rotatably connected to and coaxial with the outer cylinder, and characterized by having a radius $r_i$, wherein $r_i < r_o$ and the outer cylinder and the inner cylinder define an annulus; and, a rotatable connector connecting the outer cylinder to the inner cylinder.

A Couette device is a device in which two or more walls define an annulus and in which an apparatus can impart Couette flow to a fluid (a gas or a liquid) occupying all or part of the annulus. A "cylindrical Couette device," as the term is used herein, refers to a device comprising an outer, hollow cylinder and an inner cylinder, which define an annulus in the volume between the exterior surface of the inner cylinder and the interior surface of the outer cylinder. These surfaces may be referred to herein as "annular walls." The term "cylinder" refers to an object having a substantially circular cross-section in a plane perpendicular to the axis of the object. By rotating the outer cylinder, the inner cylinder, or both relative to one another, Couette flow can be imparted to a fluid (a gas or a liquid) occupying all or part of the annulus. The Couette device further comprises a sample inlet and a sample outlet for charging and draining the fluid from the annulus. The sample inlet and the sample outlet can be separate ports or the same port. The sample inlet can comprise a pressure regulator capable of charging the annulus to a defined pressure of the fluid. Examples of Couette devices include the cylindrical Couette device disclosed by Nenninger, U.S. Pat. No. 5,959,194.

The amount of shear generated by a Couette device can be characterized by a Reynolds number. The Reynolds number for a cylindrical Couette device, wherein the inner cylinder rotates and outer cylinder is stationary relative thereto, with a particular fluid therein can be represented as $R_e = (\omega \rho / \mu) r_i (r_o - r_i)$, wherein $\omega$ is the rotational speed, $\rho$ is the density of the fluid, $\mu$ is the dynamic viscosity of the fluid, $r_i$ is the radius of the inner cylinder, and $r_o$ is the radius of the outer cylinder. "Fully turbulent flow," as the term is used herein, refers to flow that is both non-laminar and free of vortices.

In one embodiment, the Couette device of the present invention is a cylindrical Couette device. The cylindrical Couette device will be described as a particular embodiment, but the ordinary skilled artisan having the benefit of the present disclosure will find the construction, maintenance, and use of spherical Couette devices, parallel Couette devices, and other Couette devices to be a matter of routine experimentation.

The cylindrical Couette device comprises an outer cylinder, as described above. The outer cylinder is defined by a cylindrical wall having an interior surface and an exterior surface. Affixed thereto are a top wall having an interior surface and an exterior surface and a bottom wall having an interior surface and an exterior surface. Generally, the outer cylinder, the top wall, and the bottom wall will define a pressure containment zone. Typically, in the top wall, the bottom wall, or both, there can be a mounting apparatus for mounting the inner cylinder, and a seal for sealing the joint of the inner cylinder and the top or bottom wall. As will be apparent to the skilled artisan, a cylinder will have a radius.

In one embodiment of the present invention, the shortest distance between the axis of the outer cylinder and the interior surface of the cylindrical wall can be defined as a radius $r_o$.

The outer cylinder can be fabricated from any suitable material. In one embodiment, the outer cylinder can be fabricated from a sour-fluid-resistant alloy. A "sour-fluid-resistant alloy" means a material comprising one or more metals and is resistant to corrosive materials that can be present in crude oils or other fluids. Such corrosive materials include $H_2S$, among others. In a further embodiment, the outer cylinder can be fabricated from a nickel-chromium-iron alloy, such as is commercially available as Inconel®, Inco Ltd., Toronto, Ontario. In another embodiment, the outer cylinder can be fabricated from a stainless steel.

The outer cylinder can be machined to any appropriate specification of cylindrical perfection, interior surface roughness or smoothness, or size, among other parameters that will be apparent to the skilled artisan. In one embodiment, the cylindrical perfection and interior surface roughness or smoothness are sufficient to ensure turbulence in a sample of a fluid loaded to the annulus of the cylindrical Couette device.

The cylindrical Couette device comprises an inner cylinder, as described above. The inner cylinder is defined by a cylindrical wall having an exterior surface. Affixed thereto can be a top wall having an exterior surface, a bottom wall having an exterior surface, or both. The inner cylinder will typically also comprise a portion connected to or integral with the top wall, the bottom wall, or both which is capable of coupling to a matching coupling apparatus in the top wall, the bottom wall, or both of the outer cylinder.

In one embodiment of the present invention, the inner cylinder can be rotatably connected to and coaxial with the outer cylinder. "Rotatably connected," as used herein, means that the inner cylinder is mounted to the outer cylinder in such a way that the inner cylinder, the outer cylinder, or both are free to rotate relative to one another. "Coaxial" has the meaning that the axis of the inner cylinder and the axis of the outer cylinder both lie along substantially the same line.

In one embodiment of the present invention, the inner cylinder is coupled to the top wall of the outer cylinder by one or more bearings.

In one embodiment of the present invention, the inner cylinder can comprise a heat source. The heat source can be integral with the inner cylinder or wholly or partially surrounded by other components of the inner cylinder. Exemplary heat sources include a heating cartridge and viscous heating (i.e., frictional heating generated at the boundary between the rotating cylinder and a fluid present in the annulus), among others.

In one embodiment, the heat source is a heater cylinder, defined by a cylindrical wall having an exterior surface. The heater cylinder can be connected to the outer cylinder and located in the interior of the inner cylinder. The heater cylinder will have a radius $r_h$, defined as the shortest distance between the axis of the heater cylinder and the exterior surface of the heater cylinder cylindrical wall, and $r_h < r_i$. The heater cylinder can itself define a chamber in which a heater cartridge can be located. The heater cylinder can be closed at either or both ends or open at either or both ends as a matter of routine experimentation to the skilled artisan having the benefit of the present disclosure. In one embodiment, the heater cylinder is open at one end, to allow insertion of a heater cartridge into the heater cylinder while allowing the other, closed end to form a part of the pressure containment of the Couette device. If the heater cylinder is housed within the inner cylinder, the heater cylinder can be fixed relative to the inner cylinder, fixed relative to the outer cylinder, or unfixed relative to either cylinder.

The inner cylinder can be fabricated from any suitable material. In one embodiment, the inner cylinder can be fabricated from a sour-fluid-resistant alloy, such as a nickel-chromium-iron alloy, as described above. In another embodiment, the inner cylinder can be fabricated from a stainless steel. The inner cylinder can be machined to any appropriate specification of cylindrical perfection, exterior surface roughness or smoothness, or size, among other parameters that will be apparent to the skilled artisan. In one embodiment, the cylindrical perfection and exterior surface roughness or smoothness are sufficient to ensure turbulence in a sample of a fluid loaded to the annulus of the cylindrical Couette device.

The inner cylinder will have a radius $r_i$, defined as the shortest distance between the axis of the inner cylinder and the exterior surface of the inner cylinder wall. As will be apparent to the skilled artisan from the foregoing discussion of the cylindrical Couette device geometry, $r_i < r_o$. As will be apparent to the skilled artisan, the ratio of $r_o/r_i$ can theoretically be any value greater than 1 and less than infinity. Typically, the value of $r_o/r_i$ can be in the range of from about 1.1 to about 3.0. In particular embodiments, the value of $r_o/r_i$ can be about 1.5, about 2.0, or about 2.5.

A spherical Couette device will generally be similar, with the primary differences being that the outer cylinder will instead be an outer sphere and the inner cylinder will instead be an inner sphere. A parallel Couette device will also generally be similar, with the primary differences being that the outer cylinder will instead be a first plate and the inner cylinder will instead be a second plate parallel to the first. Top and bottom end caps, as can be used in the cylindrical Couette device, can be dispensed with, replaced with functionally equivalent components, or changed in geometry in the spherical Couette device or the parallel Couette device. The outer cylinder of the cylindrical Couette device, the outer sphere of the spherical Couette device, and the first plate of the parallel Couette device can be considered homologous structures. The inner cylinder of the cylindrical Couette device, the inner sphere of the spherical Couette device, and the second plate of the parallel Couette device can be considered homologous structures.

As stated above, the outer cylinder and the inner cylinder of the cylindrical Couette device, or the homologous structures of other Couette devices, define an annulus. The annulus may also be referred to as a "pressure containment zone." An inlet and an outlet are provided, typically in the outer cylinder, such as in the top wall, bottom wall, or cylinder wall of the outer cylinder, although an inlet and an outlet in the inner cylinder are possible, to allow a fluid to be charged to the annulus and drained from the annulus. As stated above, the inlet and the outlet can be the same port or they can be different ports.

As stated above, the cylindrical Couette device comprises a rotatable connector between the inner cylinder and the outer cylinder. In one embodiment of the present invention, the rotatable connector can be a magnetic coupling to connect the inner cylinder with a prime mover, such as a motor, without physical contact. The motor can rotate a magnet array. The magnet array can provide a magnetic coupling involving a magnetic field, through the outer cylinder wall, top wall, or bottom wall, between an outer and inner set of magnets. Upon rotation of the magnet array, a torque is imparted to one cylinder relative to the other resulting in its rotation. A magnetic coupling allows the inner cylinder and the outer cylinder to rotate relative to one another without the need of a dynamic seal, allowing higher pressures of fluid in the annulus and higher rotational speeds than a dynamic seal would allow. A magnetic coupling allows the inner cylinder and the outer cylinder to rotate relative to one another with less friction than is typically found when a physical seal, such as a gasket, O-ring, or the like, is used, thus allowing more efficient operation of the cylindrical Couette device.

The rotatable connector can further comprise one or more bearings between the inner cylinder and the outer cylinder.

As stated above, the cylindrical Couette device also comprises a motor or motors capable of rotating the inner cylinder, the outer cylinder, or both relative to one another. The motor or motors can be any appropriate motor known in the art, such as an electric motor.

The Couette device of the present invention can also comprise other components. In one embodiment, the Couette device further comprises a heat exchange jacket which envelops at least a portion of the outer cylinder and has an interior surface and an exterior surface. The exterior surface of the outer cylinder and the interior surface of the heat exchange jacket define a heat exchange fluid annulus in the space therebetween. The heat exchange jacket comprises a heat exchange fluid inlet and a heat exchange fluid outlet, which can be the same port or different ports. A heat exchange fluid, which can be any fluid but is typically water, can serve to heat, cool, or maintain the temperature of the fluid inside the Couette device, and can be charged to the heat exchange fluid annulus via the heat exchange fluid inlet at a temperature at which it is desired to hold the Couette device or at a temperature and a flow rate which will keep the temperature of the Couette device at the desired temperature. Heat exchange fluid can then be drained from the heat exchange fluid annulus via the heat exchange fluid outlet. The heat exchange fluid can be at ambient pressure, reduced pressure, or elevated pressure, as appropriate depending on the heat exchange fluid and the desired temperature at which the Couette device is to be held.

In another embodiment, the Couette device further comprises one or more temperature sensors, such as one or more thermocouples or RTDs. The temperature sensor can be mounted in the inner cylinder, the outer cylinder, the top wall, the bottom wall, or two or more of the foregoing, in such a way as to report the temperature at one or more points in the inner cylinder, annulus, or outer cylinder.

In a further embodiment, the Couette device further comprises a torque sensor, such as a viscometer; or a shear sensor. The torque sensor can be mounted at any point where it can measure the torque generated in the Couette device; a convenient mounting point is on the shaft of the driving device. The shear sensor can be mounted on the inner cylinder, the outer cylinder, or both in such a way as to calculate the shear undergone by the fluid at one or more points in the annulus.

The Couette device can further comprise other sensors, such as a heat exchange fluid inlet temperature sensor, a heat exchange fluid outlet temperature sensor, a heat exchange jacket pressure sensor, heat exchange fluid inlet and outlet pressure differential sensors, a heat exchange fluid flow rate sensor, an inner cylinder rotational speed sensor, a motor rotational speed sensor, or two or more of the foregoing, among others.

In one embodiment, the Couette device further comprises a displacement fluid inlet and a displacement fluid outlet. The displacement fluid inlet allows a displacement fluid to be charged to the annulus to expel a fluid sample from the annulus via the sample outlet. The displacement fluid inlet can comprise a pressure regulator capable of charging the displacement fluid to the annulus at a defined pressure. In one embodiment, the pressure regulator can charge the displacement fluid to the annulus at a pressure substantially equal to that of the fluid sample. The displacement fluid inlet can comprise a heater, a cooling device, or both to set the temperature of the displacement fluid. In one embodiment, the heater, the cooling device, or both can set the temperature of the displacement fluid to a temperature substantially equal to that of the fluid sample.

In one embodiment, the displacement fluid is helium. In other embodiments, other inert gases, mixtures thereof, or a mixture of solution gases from the sample fluid (a "solution gas mixture"), can be used.

Generally, the displacement fluid outlet will be the same port as the sample outlet, although a separate displacement fluid outlet can be provided, such as for venting an overpressure of displacement fluid from the annulus after the fluid sample has been expelled.

In another embodiment, the Couette device further comprises a solvent inlet and a solvent outlet. The solvent inlet allows a solvent to be charged to the annulus and dissolve organic materials which may be present on the annular walls as a result of precipitation and deposition from a fluid sample. The solution so generated can be drained via the solvent outlet and thereafter subjected to further analysis via techniques and apparatus known in the art and apparent to the skilled artisan having the benefit of the present specification.

In one embodiment, the Couette device of the present invention is capable of continuous operation, that is, sample fluid is continuously charged to the annulus and is simultaneously continuously withdrawn from the annulus. The rates of fluid charge and withdrawal can be the same or they can be different; if different, the pressure of the sample will increase if the rate of fluid charge is greater than the rate of fluid withdrawal and will decrease if the rate of fluid charge is less than the rate of fluid withdrawal.

The various inlets and outlets described above can include plugs, valves, pressure regulators, or other devices capable of regulating the charging or draining of sample fluid, displacement fluid, solvent, or heat exchange fluid. The precise devices used are a matter of routine selection for one of ordinary skill in the art having the benefit of the present disclosure. A single physical port can function as one, two, three, or more of the various inlets, outlets, or both described above, as a matter of routine experimentation to the skilled artisan having the benefit of the present disclosure.

The Couette device of the present invention can also comprise a solution analysis device downstream of the solvent outlet. The solution analysis device can be a chromatograph or any other device capable of identifying, quantifying, or both particular organic compounds dissolved in the solution drained from the annulus via the solvent outlet. Exemplary solution analysis devices include, but are not limited to, gas chromatographs, high performance liquid chromatographs (HPLCs), gel permeation chromatography, nuclear magnetic resonance imagers (NMR), infrared spectroscopes, ultraviolet spectrophotometers, thin layer chromatographs, and column chromatographs, among others.

The Couette device of the present invention can also comprise one or more analysis devices which detect the presence of solids in the fluid sample. These solids can include waxes, asphaltenes, and hydrates, as well as emulsions, such as water-in-oil emulsions. The analysis devices can include viscometers, quartz crystal microbalances, ultrasonic probes, light transmittance/scattering probes, temperature sensors, and electrical conductivity sensors, among others.

The Couette device of the present invention can also comprise a composition altering device upstream of the sample inlet. A "composition altering device" is a device which can change the composition of the sample fluid. In one embodiment, the composition altering device is a continuous-flow mixer, such as a static mixer. As used herein, the term "change" refers to a controllable increase or decrease in the value of a process variable.

The Couette device can also comprise a controller, such as a computer capable of receiving inputs from the user, from a data-gathering device or devices within or around the Couette device, or both; performing calculations based on the inputs; and sending outputs to the user, to control an actuating device or devices around the Couette device, or any combination thereof. The inputs so received can include temperature, pressure, torque, cylinder rotational speed, sample composition, and deposit thickness and composition as a function of time, among others. The inputs can be received either in real time, offline, or both. The outputs so sent can be used to vary parameters of a test run via the actuating devices and report results. The parameters that can be varied can include temperature, pressure, torque, cylinder rotational speed, and sample composition, among others, and the reported results can include temperature, pressure, torque, cylinder rotational speed, sample composition, and deposit thickness and composition as a function of time, among others. The outputs can be sent either in real time, offline, or both. In addition to the controller, the Couette device can also comprise apparatus for transferring signals between the controller and any of the user, the data-gathering device or devices, and the actuating device or devices, among others. Signal transmission devices can include cables, wireless transmitters, and wireless receivers, among others.

In one embodiment, the reported results include temperature, pressure, torque, cylinder rotational speed, sample composition, surface type, surface roughness, and deposit composition.

We have discovered that Couette devices according to the present invention provide pressure and shear comparable to field conditions, to readily study the deposition tendency and extent of solids.

"Comparable to field conditions" means that the pressure, shear, composition, and other parameters generated in the Couette devices of the present invention are each substantially equal or equivalent to the pressure, shear, composition, and other parameters which a fluid can undergo in industrial-scale transport or processing. The composition of a fluid can vary as a result of injecting new materials, mixing two or more materials, changing the phase of the fluid by increasing or decreasing the temperature or pressure of the fluid, or other techniques, thus simulating industrial scale events such as gas-lift or commingling, among others.

Figure 1:
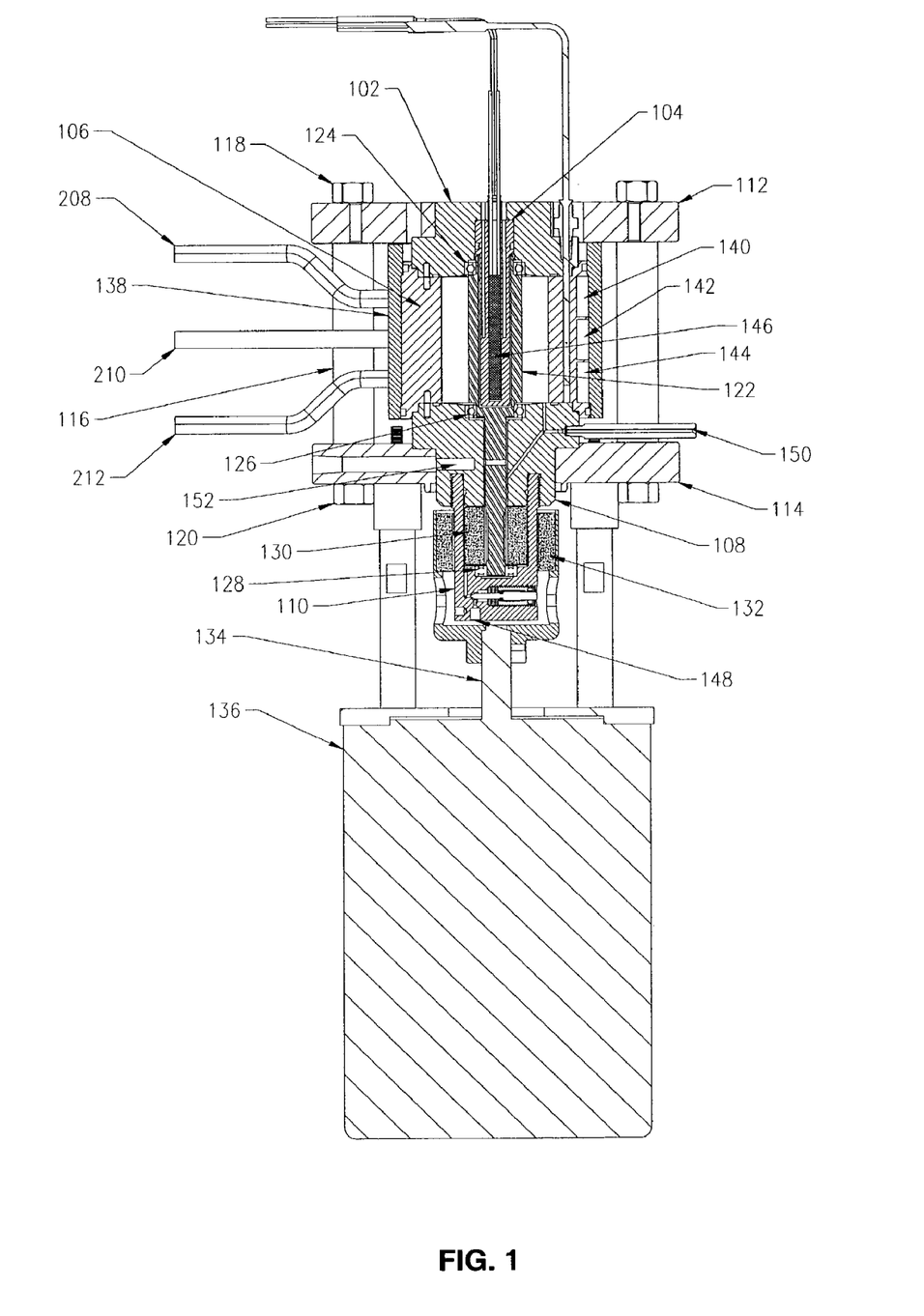
Figure 2:
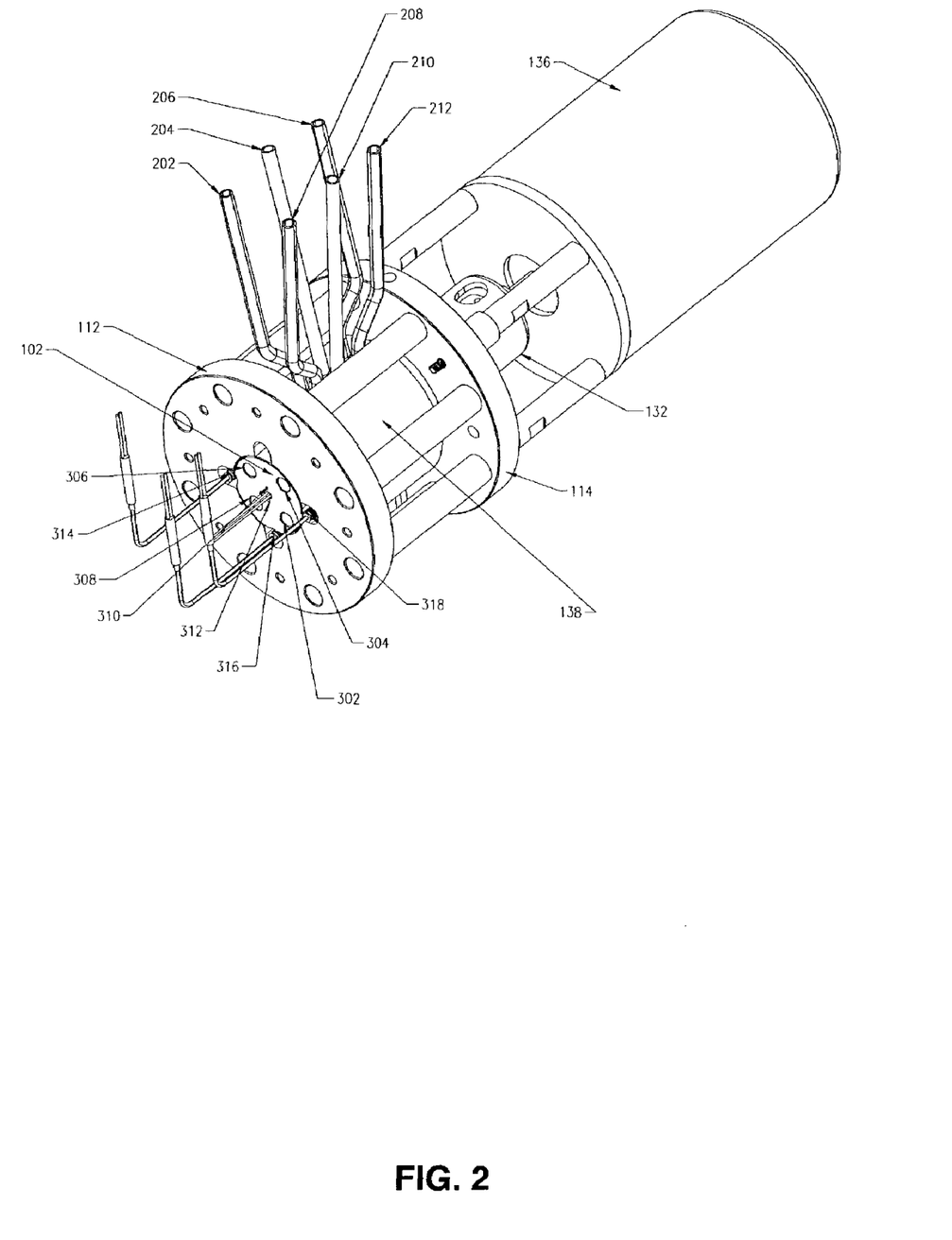
FIG. 2 shows another view of a cylindrical Couette device of the present invention.
Figure 3:
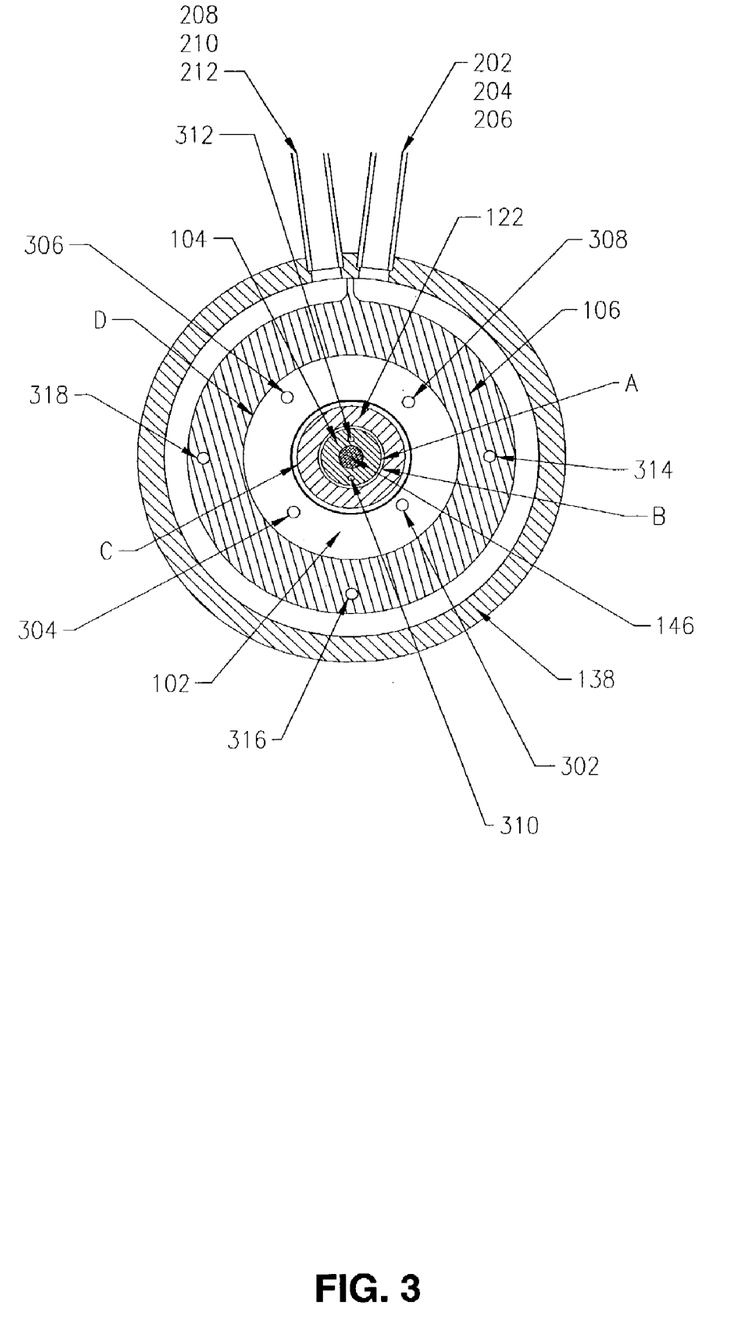
FIG. 3 shows a top-down cross-sectional view of a cylindrical Couette device of the present invention.

One exemplary embodiment of a Couette device of the present invention is shown in FIGS. 1–3. Generally, the device consists of a pressure-containing chamber within which an inner cylinder is affixed on bearings to the top and bottom walls of the cell. Rotation of the inner cylinder is driven through a magnetic coupling without the requirement for direct connection to a motor or other prime mover. This enables the cell to be operated at higher pressure than would be possible if a drive shaft were to penetrate the outer wall of the cell, in which case, a dynamic seal would be required.

Materials of construction were chosen based on operating parameters, pressure and temperature, as well as process fluid compatibility. Materials of construction and seals can be altered as necessary to meet changes in operating conditions.

Heat can be transferred to the cell through a heat cylinder wall. It can then be transferred through a small annulus to the rotating inner cylinder and subsequently to the sample fluid. The heat is then typically drawn from the cell through the outer wall into the fluid circulating through a jacket surrounding the outer cylinder. The jacket fluid can also transfer heat energy into the cell if its temperature is higher than the process fluid. There can also be further heat loss/gain, to a lesser extent, through the top and bottom walls of the cell. Also, additional heat can be generated through viscous heating caused by friction between the rotating inner cylinder and the process fluid. An insulating jacket can also be installed to minimize non-accounted heat loss (i.e., heat lost from the heat cylinder but not transferred to the circulated fluid).

The system can be instrumented as necessary to capture operating conditions and/or control the process. In this exemplary embodiment, there is provision for sensing: bulk jacket fluid inlet temperature; jacket fluid temperature for each of three chamber outlets; pressure differential between inlet and outlet of each of three jacket fluid chambers; static pressure of jacket fluid; outer wall temperature for nine locations (three radial locations, each with three axial locations within); bulk flow rate of jacket fluid; process fluid temperature at three radial locations; process fluid pressure; heater cylinder wall temperature at two radial locations; rotational speed of inner cylinder; and rotational speed of motor. The number of sensor locations is not crucial. Additional instrumentation can be added as desired. One such piece of additional instrumentation can be a torque sensor in the motor shaft, which can be used to resolve shear stress in the sample fluid at the inner cylinder wall.

Sample fluid is charged and evacuated through one or more of three ports arranged in suitable locations. Additional porting can be added, or existing porting removed, as desired.

Turning to the exemplary cylindrical Couette device of FIGS. 1–3, the boundary of the pressure containment zone is defined by the top wall 102, heater cylinder 104, outer cylinder 106, bottom wall 108, and magnetic drive cylinder 110.

The assembly is constrained by top 112 and bottom 114 retaining plates that are set apart by spacers 116 and secured by bolts 118 and nuts 120. The quantity of spacers can be altered as desired.

Seals between the following components contain the charged fluid: top wall 102 and outer cylinder 106; top wall 102 and heater cylinder 104; bottom wall 108 and outer cylinder 106; and bottom wall 108 and magnetic drive cylinder 110. The seal type and material are selected based on operating pressure, temperature and contained fluid.

Within the cell, the inner cylinder 122 is mounted on bearings 124, 126 and 128, coaxial to the outer cylinder 106, the heater cylinder 104, and the magnetic drive cylinder 110. The inner cylinder is able to rotate independently of both the outer cylinder 106 and the heater cylinder 104. A shaft is extended from the bottom of the inner cylinder to which an array of magnets 130 is secured. A similar magnet array 132 is attached, outside the pressure containment, to the shaft 134 of the motor 136.

The magnetic drive cylinder 110 is constructed of a non-magnetic alloy allowing unimpeded magnetic attraction between the outer magnet array 132 and inner magnet array 130. Through the magnet couple, a torque load can be applied to the inner cylinder 122, resulting in its rotation. The strength of the couple is a function of magnet material, number, size and arrangement.

A variable speed motor 136 is used to rotate the outer magnet array 132.

Surrounding the outer cylinder 106 is a multi-chamber (i.e., one or more chamber) circulation jacket 138 through which fluid is flowed. In one embodiment, there are three chambers; the quantity can be altered as desired. The fluid enters the jacket through inlets 202, 204, and 206, flows circumferentially around the cell through the chambers 140, 142, and 144 formed by the outer cylinder 106 and the jacket 138, and then exits the jacket through outlets 208, 210, and 212. The quantity of inlets and outlets can be altered as desired.

An internal heater 146 is confined in a cavity defined by the heater cylinder of the cell. The heater cylinder walls form a cavity, which is open to the top to allow the insertion of the heater core through the top wall 102, and to access wiring. The electric heater can be controlled using any number of temperature sensor locations as the control point. In one embodiment, a 300 W heater is used; however, this can be altered as desired. Also, in an alternative cylindrical Couette device, the heater can be directly incorporated into the inner cylinder and the heat cylinder 104 can be eliminated.

Fluid can be charged and evacuated to or from the cell through three ports 148, 150, and 302. Ports can be added or altered as desired.

Instrumentation in the device can be added or changed as necessary. In one embodiment, three thermocouple ports are as follows: 304, 306, and 308 in the top wall to allow for temperature measurement of the process fluid at three discrete radial distances; 310 and 312 in the heater cylinder wall to allow for temperature measurement within the wall at two discrete radial distances; 314, 316, and 318 in the outer wall to allow temperature measurement within the wall at three discrete radial distances; and further temperature sensors are mounted in the circulation fluid to measure both inlet and outlet temperatures. The quantity and location of sensors can be altered as desired. Also measured is the differential pressure between inlet and outlet of the circulation fluid chambers, as well as the cell pressure. In addition, the rotational speed of the inner cylinder is measured through the use of a proximity sensor 152. A torque sensor can be included, e.g., coupled to the motor shaft 134 to resolve the shear stress in the fluid at the inner cylinder wall.

In another embodiment, a device to measure deposition of the present invention comprises:

a top wall, a heater cylinder comprising a cavity, an outer cylinder coaxial with and greater in radius than the heater cylinder, a bottom wall, a magnetic drive cylinder fabricated from a nonmagnetic alloy, and one or more seals sealing the top wall and the outer cylinder; the top wall or the bottom wall and the heater cylinder; the bottom wall and the outer cylinder; and the top wall or the bottom wall and the magnetic drive cylinder, defining a pressure containment zone;

an inner cylinder (i) within the pressure containment zone, (ii) coaxial to the outer cylinder, the heater cylinder, and the magnetic drive cylinder, (iii) mounted such that the inner cylinder is able to rotate independently of both the outer cylinder and the heater cylinder, and (iv) comprising a shaft extended from the top or the bottom thereof to which an inner magnet array is secured;

a motor (i) outside the pressure containment zone, (ii) comprising a rotatable shaft to which an outer magnet array is attached, and (iii) wherein the outer magnet array has unimpeded magnetic attraction with the inner magnet array;

a circulation jacket surrounding the outer cylinder, comprising a heat exchange fluid inlet and a heat exchange fluid outlet;

an internal heater, housed in the cavity of the heater cylinder; and one or more ports to the pressure containment zone.

A Couette device of the present invention is capable of operating at conditions comparable to field conditions, including pressures, temperatures, compositions (including, for example, sour fluids), surface materials and roughnesses, and shear (i.e., fully turbulent flow) comparable to field conditions. In one embodiment, the Couette device of the present invention can operate at a pressure of at least about 15,000 psi and a temperature of at least about 200° C. In one embodiment, the Couette device can yield a Reynolds number for water of at least about 500,000. The pressure and temperature can be increased as a matter of routine experimentation for the skilled artisan having the benefit of the present disclosure.

Given such high maximum operating Reynolds numbers for water, it is possible for the sample fluid to be charged to the device while the device is generating turbulent flow, that is, flow without the presence of vortices in the annulus, and for such turbulent flow to be present throughout the run. As a result, the scale of the Couette device is not important, and a Couette device of essentially any size can be fabricated with the expectation that the results found for a particular sample under a particular set of conditions will be invariant across Couette devices of different size.

In a further embodiment, the present invention relates to an apparatus for measuring solids deposition in a fluid sample, comprising:

means for subjecting a sample of a fluid comprising solids to turbulent flow, wherein the sample has a pressure, a temperature, a composition, and is subject to a shear;

means for changing at least one of the pressure, the temperature, or the composition of the sample or the shear to which the sample is subjected; and means for measuring the deposition of the solids resulting from the change in the pressure, the temperature, the composition, or the shear.

The subjecting means can be the inner cylinder and the outer cylinder of a cylindrical Couette device, wherein the cylinders can be rotated relative to each other at a sufficiently high rotational speed to generate turbulent flow in the annulus therebetween. The sample will inherently have a pressure, a temperature, a composition, and a shear.

The changing means can be any one or more of a variety of apparatus, depending on the property of the sample to be changed. Means for changing the pressure include an inlet for introducing additional sample to the subjecting means, an outlet for regulating the passage of sample from the subjecting means, or a combination thereof, among others. Means for changing the temperature include a heat exchange fluid bath at least partially surrounding the subjecting means, wherein the temperature of the heat exchange fluid bath can be adjusted by a heater, a cooling device, or both; a heater directly providing heat to the subjecting means; a cooling device directly cooling the subjecting means; or a combination thereof, among others. Means for changing the composition include a mixer capable of adjusting the proportions of two or more subsamples relative to one another, among others. Means for changing the shear include a motor to increase or decrease the relative rotational speed of the inner cylinder and the outer cylinder, among others.

The measuring means can include a solvent washer, to dissolve deposited solids from the walls of the subjecting means; an outlet for the solution containing solvent and dissolved solids; a gas chromatograph; a high performance liquid chromatograph; a gel permeation chromatograph; a nuclear magnetic resonance imager; an infrared spectroscope; an ultraviolet spectrophotometers; a thin layer chromatograph; a column chromatograph; the walls or tubing of the apparatus where deposited solids can be visually inspected; or a combination thereof, among others.

In another embodiment, the present invention relates to a method of measuring solids deposition in a fluid sample, comprising:

charging the sample to a Couette device;

subjecting the sample to a pressure, a temperature, a surface type, a surface roughness, and a shear comparable to field conditions;

changing at least one of the pressure, temperature, composition, surface type, surface roughness, or shear of the sample; and quantifying the type and amount of solids deposited on the interior walls of the Couette device.

By "solids," as used herein, is meant one or more compounds dissolved or suspended in an industrial fluid. Solids can be organic (containing carbon) or inorganic (not containing carbon). In one embodiment, wherein the industrial fluid is crude oil, the solids can comprise one or more of asphaltenes, waxes, sulfur, or hydrates, as described above.

A fluid, as used herein, is any aqueous, organic or other liquid or gas carrying or potentially carrying materials in solution, suspension, emulsion, slurry, or other form. Any fluid used in industry can be studied according to the present method. For example, the fluid sample can be taken from a latex paint, an oil-based paint, a solvent, or other painting fluids; an aqueous or other fluid found in the food processing industry; a slurry of pulp found in the pulp and paper industry; suspensions found in the cosmetics industry; potable, semipotable, or non-potable water, either pre- or post-treatment; fluids used in cooling and processing in power generators, such as in nuclear reactors; process fluids used in, or fluid products of, the pharmaceutical industry; or crude oil or refined oil fractions from the petrochemical industry, among others. The foregoing list is not exhaustive.

In one embodiment, the fluid is a crude oil. Crude oil from many formations commonly contains solids, typically as one or more of waxes, asphaltenes, sulfur, minerals (e.g., scale), and hydrates. When crude oil is transported via pipe, such as from a formation to a wellhead via production tubing or from a wellhead or a storage vessel to a refinery via a pipeline, changes in the pressure, temperature, composition, or other parameters of the flowing crude oil can lead to deposition of solids. To clarify the terms "deposition" and "precipitation," the term deposition has often been used to describe the precipitation process. We do not use "deposition" in this way. While precipitation may be defined as the formation of a solid phase out of a liquid phase, deposition can be described as the formation and growth of a layer of the precipitated solid on a surface. Further, a necessary but not a sufficient condition for deposition is the precipitation of a solid phase from liquid solution. That is, although precipitation is a precursor to deposition, it does not necessarily ensure deposition. Moreover, whereas precipitation is mainly a function of thermodynamic variables such as composition, pressure and temperature, the deposition is also dependent on the flow hydrodynamics, heat and mass transfer, and solid-solid and surface-solid interactions. "Precipitation," as used herein, refers to the agglomeration of solids while remaining suspended in the bulk fluid fraction. "Deposition," as used herein, refers to the falling out of suspension of the agglomerated solids and the resulting coating of the agglomerated materials on the interior wall of the pipe or tubing. As stated above, deposited solids can lead to reductions in the flow rate of the crude oil or other fluid in the pipe and require expensive and time-consuming cleaning of the pipe to restore the maximum flow rate of the crude oil or other fluid. Understanding at what pressures, temperatures, and other flow parameters precipitation or deposition are likely to occur in a sample of a particular crude oil or other fluid can allow a pipe operator or other user to maintain the crude oil or other fluid at flow parameters whereat precipitation or deposition are unlikely to occur, thus minimizing reductions in the flow rate of the crude oil or other fluid.

In the method, the fluid sample can be charged to a Couette device. In one embodiment, the Couette device is a cylindrical Couette device as described above.

In one embodiment, the charging step is performed isobarically, isothermally, or both.

In one embodiment, the Couette device is stored with water in its annulus, and charging involves displacing the water with the sample. Generally, all water or any other storage liquid can be fully removed from the Couette device prior to performing later steps of the method.

Once charged to the Couette device, the sample can be subjected to a pressure, a temperature, a surface type, a surface roughness, and a shear comparable to field conditions. The pressure can be reached by a sufficiently high rate or amount of sample charging. The shear can be reached by sufficiently rapid rotation of the inner cylinder, the outer cylinder, or both relative to each other.

Subjecting the sample to a pressure, a temperature, a surface type, a surface roughness, and a shear comparable to field conditions enables more realistic simulation of flow conditions in pipe and thus the method can provide results that more accurately reflect field conditions.

After the sample is undergoing turbulent flow, one or more of the pressure, temperature, composition, a surface type, a surface roughness, or shear of the sample can be changed. In one embodiment, the shear remains sufficiently high for the sample to remain under turbulence.

The pressure can be changed by changing the rate or amount of the sample charged to the Couette device; by changing the rate of amount of the sample drained from the Couette device; or by a combination thereof.

The temperature can be changed by changing the temperature of a heat exchange fluid; by internal heating of the contents of the Couette device; or by a combination thereof. Internal heating can be performed by use of a heating cartridge, by viscous heating, or both. The temperature can be changed to different extents at different portions of the Couette device, i.e., temperature gradients can be formed or maintained.

The composition can be changed by changing the proportions of two or more subsamples from which the sample is derived; by injecting an additional amount of the sample fluid; or by changing the phase.

The surface type and surface roughness can be "changed" by performing a experimental runs in each of a plurality of Couette devices, wherein the Couette devices differ in surface type, surface roughness, or both. A single Couette device which is modified between experimental runs provides a "plurality of Couette devices," as used herein.

The shear can be changed by changing the relative rotational speed of the inner cylinder to the outer cylinder.

The various techniques for changing the parameters described above are not to be considered an exhaustive list.

As a result of the change in one or more of pressure, temperature, composition, surface type, surface roughness, or shear, dissolved solids may precipitate or deposit on the interior walls of the Couette device. During or after the changing step, the type and amount of solids deposited on the interior walls of the Couette device can be quantified.

Quantification can be performed by any appropriate technique or apparatus, such as by sensing the type and amount of solids deposited on the interior walls or by removing solids from the interior walls and thereafter quantifying the type and amount. "Quantifying" is used herein to refer to both qualitative analysis, that is, whether particular solids, such as particular waxes, particular asphaltenes, or particular hydrates are present, and quantitative analysis, that is, what quantities of particular solids, such as particular waxes, particular asphaltenes, or particular hydrates are present. Techniques for quantification include, but are not limited to, gas chromatography, high performance liquid chromatography (HPLC), gel permeation chromatography, nuclear magnetic resonance (NMR), infrared spectroscopy, ultraviolet spectrophotometry, thin layer chromatography, and column chromatography, among others.

In one embodiment, the method further comprises draining the sample from the Couette device. This can facilitate quantification by allowing deposited solids to be quantified in the device or by allowing deposited solids to be removed separately from the sample. The sample can be drained by gravity, by forced expulsion by application of a displacement fluid, such as helium, or other techniques.

In one embodiment, in which the method comprises draining the sample, the quantifying step comprises rinsing the interior walls with a solvent. The use of the solvent allows solids to be dissolved in the solvent. The resulting solution can then be extracted from the device and subjected to quantification, as described above.

The method can be performed, depending on the structure of the Couette device and the user's discretion, as a batch (or closed) process, a semibatch process, or a continuous (or open) process. A continuous process has the advantage of more closely simulating flow conditions in a pipe.

In a further embodiment, the present invention relates to a method of measuring an emulsion in a sample of a fluid, comprising:

charging the sample to a Couette device;

subjecting the sample to a pressure, a temperature, and a shear comparable to field conditions;

changing at least one of the pressure, temperature, composition, or shear of the sample; and quantifying the type and amount of the emulsion in the sample.

Emulsions, such as water-in-oil emulsions, can exist in fluid samples and can interfere with flow of the fluid in production tubing or pipeline or with fluid processing at a wellhead, a refinery, or a similar location, either as such or after undergoing a phase separation from other phases. Quantifying emulsions can be helpful in understanding the flow parameters of a fluid sample and improving handling of the fluid.

Generally, the charging step, the subjecting step, and the changing step are similar to those for the method of studying solids precipitation and deposition, as described above. In the quantifying step, the type and amount of the emulsion can be measured by the use of viscometers, chromatography, or other techniques in measuring the fluid sample or a phase separated therefrom.

The foregoing description has demonstrated particular embodiments of the invention. It should be appreciated by those of skill in the art that the techniques and apparatus disclosed herein function well in the practice of the invention. However, those of skill in the art should, in light of the present disclosure, appreciate that many changes can be made in the specific embodiments which are disclosed and still obtain a like or similar result without departing from the spirit and scope of the invention.

All of the apparatus and methods disclosed and claimed herein can be made and executed without undue experimentation in light of the present disclosure. While the compositions and methods of this invention have been described in terms of preferred embodiments, it will be apparent to those of skill in the art that variations may be applied to the apparatus and methods and in the steps or in the sequence of steps of the methods described herein without departing from the concept, spirit and scope of the invention. All such variations apparent to those skilled in the art are deemed to be within the spirit, scope and concept of the invention as defined by the appended claims.

What is claimed is:

1. A method of measuring solids deposition from a fluid sample, comprising:
    charging the sample of initial composition to a Couette device having interior walls, wherein the Couette device comprises an outer cylinder and an inner cylinder which define an annulus in the volume between the exterior surface of the inner cylinder and the interior surface of the outer cylinder, and wherein the fluid sample is contained within the annulus;
    subjecting the sample in the Couette device to an initial pressure, an initial temperature, an initial shear, an initial surface type, and an initial surface roughness while the inner cylinder rotates relative to the outer cylinder via a magnetic coupling with a prime mover and imparts Couette flow to the fluid sample;
    changing at least one of the pressure, temperature, composition, or shear of the sample, and at least one of the surface type or surface roughness of the device; and
    quantifying deposits on the interior walls of the Couette device.

2. The method of claim 1, wherein the charging step is performed isobarically, isothermally, or both.

3. The method of claim 1, further comprising
    draining the sample from the Couette device; and wherein the quantifying step comprises rinsing the interior walls with a solvent.

4. The method of claim 3, wherein the draining step comprises the use of an inert gas or a solution gas mixture to expel the sample.

5. The method of claim 1, wherein the solids are organic.

6. The method of claim 5, wherein the solids comprise one or more of asphaltene, wax, or hydrate.

7. The method of claim 1,
    wherein the solids are inorganic.

8. The method of claim 7, wherein tie solids comprise sulfur, scale, or both.

9. The method of claim 1, wherein the method is performed as a batch process.

10. The method of claim 1,
    wherein the method is performed as a semibatch process.

11. The method of claim 1,
    wherein the method is performed as a continuous process.

12. A method of measuring an emulsion in a fluid sample, comprising:
    charging the sample to a Couette device that comprises an outer cylinder and an inner cylinder which define an annulus in the volume between the exterior surface of the inner cylinder and the interior surface of the outer cylinder, and wherein the fluid sample is contained within the annulus;
    subjecting the sample in the Couette device to a pressure, a temperature, and a shear comparable to field conditions and to a surface type and a surface roughness while the inner cylinder rotates relative to the outer cylinder and imparts Couette flow to the fluid sample;
    changing at least one of the pressure, temperature, composition, or shear of the sample, and at least one of the surface type or surface roughness of the device; and
    quantifying the type and amount of the emulsion in the sample.

13. The method of claim 12, wherein the Couette device is a cylindrical Couette.

14. The method of claim 12, wherein the charging step is performed isobarically, isothermally, or both.

15. A method of measuring an emulsion in a fluid sample, comprising:
    charging the sample to a Couette device;
    subjecting the sample in the Couette device to a pressure, a temperature, a shear, a surface type and a surface roughness comparable to field conditions;
    changing at least one of the pressure, temperature, composition, and shear of the sample, and a least one of surface type and the surface roughness; and
    quantifying the type and amount of the emulsion in the sample.

16. An apparatus for measuring solids deposition in a fluid sample, comprising:
    means for subjecting a sample of a fluid comprising solids to turbulent flow, wherein the sample has a pressure, a temperature, a composition, and is subject to a shear, wherein the means comprise a Couette device having an outer cylinder and an inner cylinder which define an annulus in the volume between the exterior surface of the inner cylinder and the interior surface of the outer cylinder, and wherein the fluid sample is contained within the annulus, and wherein the fluid sample is subjected to a surface type and a surface roughness;
    means for magnetically coupling the inner cylinder with a prime mover for rotating the inner cylinder;
    means for changing at least one of the pressure, the temperature, or the composition of the sample or the shear to which the sample is subjected, and at least one of the surface type and surface roughness while the inner cylinder rotates relative to the outer cylinder and imparts Couette flow to the fluid sample; and
    means for measuring the deposition of the solids resulting from the change in the pressure, the temperature, the composition, or the shear, and in the surface type or surface roughness.

* * * * *